| United States Patent [19] | [11] 4,010,259 |
| Johansson | [45] Mar. 1, 1977 |

[54] DISINFECTANTS CONTAINING IODINE COMPLEXED TO A HYDROPHILIC ORGANIC CARRIER

[76] Inventor: J. A. Olof Johansson, Ejdervagen 14, Veberod, Sweden

[22] Filed: July 17, 1975

[21] Appl. No.: 596,725

[52] U.S. Cl. .................. 424/150; 424/78; 424/180; 424/343
[51] Int. Cl.² .......................... A61L 13/00
[58] Field of Search .................. 424/150

[56] References Cited
UNITED STATES PATENTS

| 2,022,729 | 12/1935 | Malisoff | 424/150 X |
| 2,567,584 | 9/1951 | Thomas | 424/150 |
| 3,728,449 | 4/1973 | Cantor et al. | 424/150 |

FOREIGN PATENTS OR APPLICATIONS

| 617,654 | 4/1961 | Canada | 424/150 |
| 617,655 | 4/1961 | Canada | 424/150 |
| 169,293 | 3/1958 | Sweden | |
| 923,114 | 4/1963 | United Kingdom | |

*Primary Examiner*—Leonard Schenkman
*Attorney, Agent, or Firm*—Bacon & Thomas

[57] ABSTRACT

The present invention relates to a disinfectant of the so-called iodophor-type, i.e. wherein iodine is complexed to a carrier. In accordance with the invention iodine is complexed to a carrier forming a three-dimensional lattice, kept together by covalent bonds, and being insoluble in water, but capable of swelling in water to form a gel. The new iodophor according to the invention can be used for technical, cosmetical and medical disinfection.

7 Claims, No Drawings

DISINFECTANTS CONTAINING IODINE COMPLEXED TO A HYDROPHILIC ORGANIC CARRIER

The present invention relates to a new disinfectant of the so-called iodophor type and to a method of preparing the new disinfectant.

Iodine in aqueous-alcoholic solutions has for a long time been used as a disinfectant. Iodine has an excellent and rapid anti-microbial effect with a broad spectrum of activity, and acquired resistance to iodine does not occur. However, iodine in the form of aqueous-alcoholic solutions and the like has many disadvantages such as poor stability, high chemical reactivity, unpleasant odor, etc., and it also discolors, irritates and often injures skin and wounds when used for treating biologic tissues.

It has been attempted to eliminate the disadvantages of such iodine solutions by complexing iodine to water soluble organic carries such as polyvinylpyrrolidone and the like. Water soluble complexes of this type, which are usually called iodophors, have been known for a long time (see e.g. Swedish Pat. No. 191,385, German Auslegeschrift No. 1,171,112 and French Pat. No. 2,128,082), and they lack some of the disadvantages of iodine solutions while at the same time essentially retaining the anti-microbial activity of iodine. The known water soluble iodophors are usually prepared by treating an aqueous solution of the carrier with an iodine solution.

Although the development of water soluble iodophors meant an important progress in the art compared to the conventional iodine solutions, the soluble iodophors still have many drawbacks and limitations relating to the preparation and use thereof. Since the products are soluble in water, the purification in connection with the preparation thereof is complicated, and it is necessary to make use of precipitation procedures involving cost consuming recovery of solvents and resulting in reduced yields. In connection with skin and wound disinfection also soluble iodophors may cause skin and wound irritation, as the solvent may evaporate and leave released iodine in direct contact with the skin or wounds in the form of tiny crystals. Furthermore, the soluble iodophors release iodine too rapidly for the most applications, the released iodine being consumed too rapidly due to its reactivity with different types of substances. As a consequence thereof the disinfecting and sterilizing effect of the water soluble iodophors ceases too rapidly in many cases.

The water soluble isodophors are usually dissolved in a treating liquid, which is applied to the objects to be disinfected. After the iodophor has excerted its anti-microbial effect by releasing iodine, the treating liquid containing the soluble carrier — and possibly residual iodophor — is discarded. This leads to increased costs and environmental contamination. Further more, the liquid form as such is a limiting factor in many cases.

Attempts have also been made to absorb/adsorb water soluble iodophors to different soluble and insoluble inorganic materials such as metal salts, clay, talc, etc. in order to obtain soluble iodophors in powder form (see e.g. Danish Pat. No. 89,457). However, the inorganic materials used are unsuitable from a physiological viewpoint (see e.g. Deutsche Medizinische Wochenschrift, Vol. 76, p. 394–397). In addition thereto the above-mentioned drawbacks and limitations of soluble iodophors remain.

According to another attempt to improve the properties of water soluble iodophors, the iodophors have been embedded in a polyethylene or polypropylene polymer. In this manner it has been possible to suppress the release of iodine and to obtain a more extended germicidal effect. However, the above-mentioned drawbacks of soluble iodophors, especially in connection with the preparation, remain. Furthermore, the polyethylene or polypropylene polymer used for embedding the iodophors is not hydrophilic and also tissue extraneous, which highly limits the applicability of such embedded iodophors.

Thus, there is a great need for improved iodine preparations, which have the excellent anti-microbial properties of iodine without suffering from the drawbacks and limitations of the known iodine solutions and water soluble iodophors.

It is an object of the present invention to provide a new type of iodophors, which are useful as effective and versatile disinfectants, are very stable and easy to prepare, handle and store, permit a controlled release of iodine, and in addition thereto are free from smell and can be regenerated after use.

The iodophors according to the invention are characterized in that the iodine is complex bonded to a hydrophilic organic carrier, which forms a three dimensional lattice, kept together by covalent bonds, and which is insoluble in water, but capable of swelling in water to form a gel.

The water insoluble, gel-forming hydrophilic iodophor according to the invention can be prepared by complexing iodine to a hydrophilic organic carrier having the above-mentioned properties.

The carriers used for the preparation of the iodophors according to the invention are either previously known or can be prepared in analogy with the preparation of the known gel-forming products. The carrier is prepared by a polymerisation/cross-linking reaction of a polyhydroxylic organic substance by means of a bifunctional organic cross-linking agent of the type Y-R-Z, wherein Y and Z each represent epoxy groups or halogen atoms and R is an organic residue. In this polymerisation reaction each of the functional groups Y and Z react with a hydroxy group of the polyhydroxylic organic material to form ether bonds. The linking reaction has to proceed so far that the formed polymer becomes insoluble in water, but capable of absorbing water under swelling.

The polyhydroxylic starting material can consist of many different types of organic materials of varying molecular weight, which contain several hydroxy groups and are capable of forming a water insoluble, but water swellable gel by the formation of intermolecular ether bridges. Starch of varying average molecular weight (as well as different degradation products thereof) have proved to be very suitable starting materials, but also other polysaccharides such as dextran, cellulose and the like, as well as synthetic polyhydroxylic polymers such as polyvinyl alcohol of varying molecular weight can be used with good results. Other suitable starting materials are low molecular polyhydroxylic substances, for example mono- and di-saccharides such as saccharose, lactose, maltose, etc., and sugar alcohols such as sorbitol. The polyhydroxylic starting materials can also be substituted with anionic, cationic or non-ionic groups. By suitable substitution of the starting material it is possible to prepare carriers (and subsequently iodophors according to the invention) having also ion exchange properties. Carboxylic and sulphonic acid groups, and amino groups are examples of acid and basic groups useful for this purpose. Examples of suitably substituted polyhydroxylic starting materials are dextran, dextrin and starch substituted with carboxymethyl-, hydroxyethyl-, hydroxypropyl-, diethylaminoethyl-groups and the like. Said groups can also be introduced into the cross-linked water-insoluble carrier by means of known methods (see e.g. Swedish Pat. No. 204 906). The ion exchange capacity of the carrier and the iodophor according to the invention may range up to about 5 meq/g.

The cross-linking agent used for the polymerisation reaction is usually a bi-functional glycerol derivative such as epichloro hydrine, dichloro hydrine, epibromo hydrine, dibromo hydrine and the like, but also other bi-functional agents capable of forming ether bridges can be used, for example 1:2/3:4-diepoxybutane, diepoxy propylether, diepoxy propylethers of ethylene glycol, propylene glycol and polyethylene glycol, and the like. In general, aliphatic epoxy- resp. halogen-epoxy compounds containing carbon, hydrogen, oxygen, but lacking dissociatable groups can be used.

By the reaction between hydroxy groups of the polyhydroxylic organic substance and the bi-functional cross-linking agent molecules of the polyhydroxylic starting material are linked together by the formation of ether bonds of the type $R_1 — O — X — O — R_2$, wherein $R_1$ and $R_2$ represent molecules of the starting material, minus one hydroxy group, and X is the link formed by the bi-functional cross-linking agent. When for example epichloro hydrine is used as the linking agent the following reaction occurs:

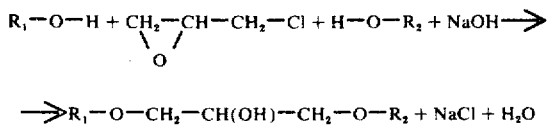

To prepare a carrier, which is insoluble, but capable of swelling in water, a great number of such linking bridges are usually required, but the necessary degree of cross-linking is, of course, also dependent on the particular starting material used, the molecular weight being the major descisive factor.

The polymerisation reaction is preferably carried out in a suitable solvent, which is capable of dissolving one or more of the reactants. The reaction is catalyzed by alkaline substances, such as hydroxides of alkaline and alkaline earth metals. Quaternary and tertiary amines are other examples of suitable alkaline catalysts. The reaction is preferably carried out in aqueous solution. When the bi-functional linking agent contains an active halogen atom, for example halogen hydrines, the corresponding hydrogen halide is formed during the reaction, and in this case an additional amount of alkaline substance must also be added to neutralize the formed hydrogen halide.

The reaction is preferably carried out at elevated temperatures, a suitable temperature interval ranging from about 50° to about 90° C. The reaction can, for example, be carried out as bulk polymerisation or emulsion polymerisation in an inert solvent such as toluene. In the emulsion polymerisation a two phase system is formed by the reaction mixture and the inert solvent respectively. The particle size of the reaction product can be controlled by, for example, variation of the concentration of stabiliser solution and the stirring speed and the design of the reaction vessel. When bulk polymerisation is used the particle size is mainly controlled by mechanical degradation such as grindning. Due to the reduced rate of diffusion it is more difficult to purify carriers of larger particle size.

The carrier is preferably purified by means of conventional methods such as washing, suction filtration or centrifugation. The washing agent is preferably water and/or an organic solvent such as ethanol. As impurities are often mechanically enclosed in the unswelled carrier, it is preferred to use at least a certain amount of a swelling agent, preferably water, in order to facilitate the purification.

The swelling capacity of the carrier (and of the iodophor prepared thereof) can be controlled by variation of the reaction conditions and the choice of starting materials. The swelling capacity, which is a measure of the ability of the carrier resp. the iodophor to take up a swelling agent such as water, is in this description defined as the gel volume (in ml) obtained when 1 g of the dry gel is completely swelled in the resp. swelling agent. When all other conditions are kept constant the swelling capacity of the carrier is proportional to the amount of solvent and inversely proportional to the amount of bi-functional organic linking agent (i.e. the degree of cross-linking) and the molecular weight of the polyhydroxylic starting material. The water swelling capacity can be decreased by substitution of the hydroxyl groups of the carrier with non-ionic groups such as hydroxy ethyl and hydroxy propyl groups. The swelling capacity in organic solvents such as ethanol is at the same time increased. The water swelling capacity of the iodophors according to the invention resp. of the carriers used for the preparation thereof can vary considerably, e.g. from about 2 to about 100 ml/g.

The properties of the new iodophors according to the invention do not only depend on the properties of the carrier used for the preparation thereof, but also of the iodine contents of the iodophor. The ability of the carrier to reversely complex iodine resp. of the corresponding iodophor to release iodine is mainly decided by the specific carrier material, its swelling capacity, the type and degree of possible substituents, by the iodine concentration during the complexing reaction, and by the particle size. A low swelling capacity of the carrier, i.e. a great number of introduced ether links, reduces the iodine complexing capacity as the molecular chains are in this case fixed to a greater extent. When using the same carrier the iodine complexing capacity can be reduced by decreasing the swelling capacity and increasing the particle size. Most types of carriers are capable of binding up to about 5 or 10 % of iodine, based on the dry weight of the iodophor, which is sufficient for the most disinfection purposes. By using a carrier of a suitable material having a high swelling capacity and securing a high iodine concentration in the complexing reaction, it is, however, possible to prepare iodophors having a considerably higher iodine content, e.g. up to about 20 %.

As mentioned above the new iodophors according to the invention can be prepared from a commercially available carrier, but it is also possible to carry out the complexing reaction in connection with the preparation of the carrier. When using a dry carrier as the starting material it should preferably be swelled before the reaction with iodine to facilitate the diffusion of iodine into the carrier particles. It is preferred to use more swelling agent than the amount necessary for completely swelling the carrier in order to facilitate the homogenizing process and promote the complexing reaction with iodine. Although water is the preferred swelling agent also other solvents or mixtures of solvents capable of at least partly swelling the carrier can be used, especially if the carrier is substituted with non-ionic groups. Thus, the iodine complexing reaction can, for example, be carried out in the presence of such organic solvents as dimethylsulphoxide, formamide, glycol, lower alcohols, acetone, etc., but the reaction mixture preferably contains some water.

When the complexing reaction is carried out in connection with the preparation of the carrier, the latter is preferably purified, but not dried before the treatment with iodine. Also in this case it is preferred to use an excess of swelling agent as the reaction medium for the iodine complexing reaction.

Although it is possible to add the iodine in solid or gas form for the complexing reaction between the carrier and iodine, it is preferred to dissolve iodine in a suitable solvent, preferably ethanol or an ethanol/water mixture. Any solvent capable of dissolving iodine (partly or completely) and being inert to the carrier can be used. When preparing the iodine solution it is preferred to use the least possible amount of organic solvent, as such solvents may shrink the carrier and thereby make the diffusion of iodine into the carrier particles more difficult. The temperature and the pressure of the reaction are no critical factors. As the complexing reaction readily occurs already at the ambient temperature and normal pressure these conditions are preferred for the sake of simplicity. The reaction can, however, be accelerated by slight heating. Temperatures above about 50° should, however, be avoided.

After the complexing reaction has been terminated the iodophor gel formed is separated from the reaction medium by, for example, suction filtration. The iodophor gel can possibly also be washed and/or dried in the usual manner and possibly also be disintegrated mechanically and sieved to the desired particle size. By cancelling the washing step or by only carefully washing the crude gel, the iodophor will in addition to complex bonded iodine also contain iodine which is only adsorbed/absorbed to the carrier and can easily be released. Such iodophors, which are also comprised by the invention, are preferably used when a high initial concentration of iodine is desired.

An interesting characteristic of the new iodophors according to the invention is that they contain iodine, which is reversibly complex bonded to the carrier, which is insoluble in water. It is thus possible to regenerate the carrier by complexing it with fresh iodine after the initially complexed iodine has been consumed. The regeneration can be carried out in analogy with the preparation of the iodophor, e.g. by treatment of the iodine depleted iodophor with an iodine solution.

As is apparent from the foregoing description and also from the following specific examples the physical and chemcial properties of the iodophors can be varied considerably within the scope of the invention, and as a consequence thereof it is possible to adapt the properties of the iodophor to the needs and desires in the specific case. The new iodophors can also be used either in the dry particulate (bead) form or in the form of a gel of variable viscosity, prepared by swelling the dry iodophor in a suitable swelling agent.

The new iodophors according to the invention can be used as disinfectants for the most varying purposes, cosmetical and pharmaceutical as well as technical. Iodophors in powder form can, for example, be used for spray disinfection of large surfaces such as locals and difficultly excessible surfaces in general. Because of the hydrophilic properties the iodophors are capable of absorbing water and moisture. As a consequence the powdery iodophor sticks to the treated surface and can excert its germicidal activity for an extended period of time thanks to the gradual release of iodine. When swelled in water the iodophors according to the invention can, for example, be used for the disinfection of microbially contaminated water in e.g. swimming pools, cooling tower systems and the like, and for the disinfection of equipment for the production, transportation and storing of such commodities as milk, wine and beer. For such technical applications the objects to be disinfected can be treated with a liquid such as water containing an effective amount of the iodophor. After the treatment the carrier, with possible residual iodine, can be recovered by passing the treating liquid through a filter, where the carrier, which is insoluble in water, is recovered and may be regenerated. Alternatively, the treating liquid can be passed through a filter formed by an iodophor gel, which progressively releases germicidal iodine to the treating liquid. When used as filters the iodophors preferably have a relatively large particle size — for example a dry particle size of up to about 1 mm and possibly even larger — in order to reduce the flow resistance through the filter. The iodophors according to the invention can also be used for the same purposes as the carrier used as starting material, e.g. for carrying out ion exchange or gel chromatography, the treated material at the same time being disinfected.

The iodophors according to the invention can also advantageously be used as an anti-microbial component in chemical -technical, cosmetical and pharmaceutical preparations such as baby powder, foot powder, body deodorants, different types of cleaning compositions, skin creams, and the like, the iodophors being used as powder or in gel form depending on nature of the composition.

The iodophors according to the invention can also with excellent results be used for the disinfection of skin and wounds and for preventing so-called hospital infections. As the iodophors according to the invention are hydrophilic and liquid absorbing they are especially suitable for the disinfection of fluid releasing wounds such as burning wounds. Iodophors in the form of a viscous gel are especially suitable for the disinfection of difficulty excessible infected areas such as wound pockets and fistulas, and e.g. for vaginal disinfection. When used for cosmetical and medical purposes the iodophors preferably have a relatively small particle size, e.g. from about 0.01 to about 0.50 mm.

As the optimal anti-microbial effect of iodine occurs at a slightly acidic pH, it is in may cases advantageous to use iodophors substituted with acidic groups. Suitable substituents for cosmetical and medical applications are, for example, carboxymethyl groups, which make the iodophor slightly acidic. For purely technical applications it may in certain cases be advantageous to use iodophors being strong cation exchangers, substituted with groups such as sulphoethyl groups. Weakly acidic iodophors are especially useful for the treatment of skin, wounds and other surfaces of an alkaline nature. It is, of course, also possible to use the iodophors according to the invention in combination with a suitable acidic component.

The iodine contents and the rate of release of iodine are, of course, adapted to the needs are requirements in each case. As a general rule a relatively low proportion of iodine (for example from about 100 ppm to about 0.5 %) is usually sufficient for e.g. skin and wound disinfection, whereas higher proportions of iodine, which is released as uniformly as possible over a long period of time, are preferred for many technical applications.

The new iodophors according to the invention can be used in practically every situation, where an efficient germicidal effect is desired. Thus, many other applications than those especially mentioned above are obvious to a person skilled in the art.

The invention will be further described in the following specific examples, which are only illustrative and not intended to limit the scope of the invention. The stabiliser solution referred to in the Examples was a toluene solution of a mixture of mono- and di-esters of ortho phosphoric acid (GAC PE 510, sold by GAF Corporation, U.S.A.). The solution contained 14 g of ortho phosphoric acid esters per kg of toluene. The (total) iodine content was determined by the Schoniger standard method. The release of iodine was determined by an extraction method, wherein water was added to a certain amount of the dry iodophor to form a mixture of 100 ml, which was shaken for 2 hours. After sedimentation the iodine content of the supernatant was determined and the amount of released iodine (expressed as % by weight of the total iodine content) was calculated. In some cases this procedure was repeated, fresh water being added (to 100 ml) to the sedimented gel after each extraction. Each Example indicates the amount of dry iodophor used, the number of extractions and the percentage of iodine released in each extraction.

EXAMPLE 1

500 g of commercial dextrin were dissolved in 500 ml of 3.10 H sodium hydroxide containing 5 g of sodium borohydride. 700 ml of stabilizer solution were placed in a 3-necked 2 l round-flask. The stirring speed was adjusted to 200 rpm and the dextrin solution was added slowly. 100 ml of epichlorohydrin were added after 30 minutes and the reaction was continued for 5 h at 70° C. The reaction product was purified as follows:

8 l of water were added to the reaction product, while stirring. After sedimentation of the water insoluble gel-product, the supernatant (which contained a small amount of non-sedimented product) was decanted off. Another 8 l of water were added, while stirring, and the mixture was neutralized with 2 N HCl to a pH of 6.5. The product was allowed to sediment and the supernatant was decanted. The washing procedure was repeated three times with the same amount of water. After the last washing step the product was filtered off. 1 l of acetone was added to the drip-dry gel, which was then treated with a solution of 4 g of iodine in 50 ml of ethanol (95 vol.%). The reaction mixture was stirred for 60 minutes at room temperature (23° C). The iodophor gel obtained was filtered off and then dried for 15 hours at room temperature and for 48 hours at 40° C.

Yield: 485 g. Analysis: 0.33 % iodine and 4.9 % moisture; swelling capacity: 6.6 ml/g.

EXAMPLE 2

The procedure of Example 1 was repeated using 400 g of dextrin, 400 ml of 3.10 N sodium hydroxide, 5 g of sodium borohydride, 700 ml of stabilizer solution, 80 ml of epichlorohydrin and 25 g of iodine in 200 ml of ethanol.

Yield: 352 g. Analysis: 1.22 % iodine and 5.52 % moisture; swelling capacity: 6.0 ml/g; Extraction test: 3.01 g;
  first extraction — 31 %
  second extraction — 12.3 %
  third extraction — 4.1 %
Particle size distribution:
  $> 500\ \mu$ 14 %
  $300 - 500\ \mu$ 41 %
  $100 - 300\ \mu$ 33 %
  $<100\ \mu$ 12 %

EXAMPLE 3

The procedure of Example 1 was repeated using 400 g of starch (average molecular weight 44,000), 500 ml of 2.4 N sodium hydroxide, 3 g of sodium borohydride, 800 ml of stabilizer solution, 80 ml of epichlorohydrin and 5 g of iodine in 50 ml of ethanol.

Yield: 393 g. Analysis: 0.46 % iodine and 6.6 % moisture; swelling capacity: 5.0 ml/g; extraction test: 4.00 - 1 extraction — 53 %.

EXAMPLE 4

The procedure of Example 1 was repeated using 400 g of sodium carboxymethyl starch (having a substitution degree of 0.25 carboxymethyl groups per glucose unit), 500 ml of 2.12 N sodium hydroxide, 1000 ml of stabilizer solution, 80 ml of epichlorohydrin and 10 g of iodine dissolved in 100 ml of ethanol.

Yield: 401 g. Analysis: 0.55 % iodine and 3.72 % moisture; swelling capacity: 5.6 ml/g; ion exchange capacity: 1.26 meq/g; extraction test: 4.01 g — 1 extraction — 41 %.

Before the reaction with iodine the carrier was transformed into the acid form by treatment with HCl.

EXAMPLE 5

The procedure of Example 4 was repeated using 400 g of carboxymethyl starch, 500 ml of 4.65 N sodium hydroxide, 1000 ml of stabilizer solution, 225 g 1,3-dibromohydrin and 2.5 g of iodine in 25 ml of ethanol.

Yield: 408 g. Analysis: 0.31 % iodine and 9.19 % moisture; swelling capacity: 5.6 ml/g; ion exchange capacity: 1.23 meq/g; extraction test: 4.01 g — 1 extraction — 71 %.

Before the reaction with iodine the carrier was transformed into the acid form by treatment with HCl.

EXAMPLE 6

The procedure of Example 1 was repeated using 100 g of sorbitol (Merck, Sorbit Griessform DAB 7), 80 g of a sodium hydroxide solution (50 % by weight), 150 ml of stabilizer solution, 75 ml of epichlorohydrin and 5 g of iodine in 50 ml of ethanol.

Yield: 33 g. Analysis: 0.46 % iodine and 5.32 % moisture; swelling capacity: 11.4 ml/g; extraction test: 2.01 g — 1 extraction — 28 %.

EXAMPLE 7

The procedure of Example 1 was repeated using 100 g of saccharose, 124 ml of 8.1 N sodium hydroxide, 200 ml of stabilizer solution, 75 ml of epichlorohydrin and 4 g of iodine in 50 ml of ethanol.

Yield: 75 g. Analysis: 0.63 % iodine and 9.28 % moisture; swelling capacity: 8.0 ml/g; extraction test: 3.01 g — 1 extraction — 46 %.

EXAMPLE 8

The procedure of Example 1 was repeated using 44,6 g of polyvinyl alcohol having an average molecular weight of 72,000 (Polyviol W 28/20, available from Wacker-Chemie, West Germany), 270 ml of 0.5 N sodium hydroxide, 300 ml of stabilizer solution, 12.5 g of 1,2; 3,4-diepoxybutane and 5 g of iodine in 50 ml of ethanol.

Yield: 22 g. Analysis: 0.25 % iodine and 3.90 % moisture; swelling capacity: 10.6 ml/g; extraction test: 2.37 g — 1 extraction — 16 %.

EXAMPLE 9

750 g of commercially available dextran gel (Sephadex G-25, Pharmacia Fine Chemicals, Uppsala, Sweden) having a particle size of 100 - 300 $\mu$ and a swelling capacity of 2.47 g/g were swelled in 5750 ml of water, while stirring. A solution of 62.5 g of iodine in 500 ml of ethanol was added to the swelled gel. The reaction mixture was stirred for 2 h at 35° C. The iodophor gel obtained was filtered off and washed with 600 ml of water and then dried at room temperature for 15 h and subsequently at 40° C for 48 h.

Yield: 755 g. Analysis: 2.39 % iodine and 10.03 % moisture; swelling capacity: 5.0 ml/g; extraction test: 5.01 g — 1 extraction — 15.3 %.

EXAMPLE 10

The procedure of Example 9 was repeated using 225 g of Sephadex G-25, 1075 ml of water, 600 ml of aceton and 5 g of iodine in 50 ml of ethanol.

Yield: 222 g. Analysis: 0.20 % iodine and 4.44 % moisture; swelling capacity: 5.2 ml/g.

EXAMPLE 11

100 g of a commercially available dextran gel (Sephadex G-150, Pharmacia Fine Chemicals, Uppsala, Sweden) having a particle size of 40 - 120 $\mu$ and a swelling capacity of 15 g/g were swelled in 1500 ml of water and 500 ml of acetone. A solution of 8.35 g of iodine in 100 ml of ethanol was added to the swelled gel. The reaction mixture was stirred for 30 minutes at room temperature. The product was filtered off and then dried at room temperature for 15 h and then at 40° for 48 h.

Yield: 102 g. analysis: 0.53 % iodine and 8.88 % moisture; swelling capacity: 41 ml/g; extraction test: 1.01 g — 1 extraction — 85 %.

EXAMPLE 12

100 g of a commercially available dextran gel substituted with diethylaminoethyl groups (DEAE-Sephadex A-25, Pharmacia Fine Chemicals, Uppsala, Sweden) having a particle size of 40 - 120 $\mu$ and an anion exchange capacity of 3.5 meq/g were allowed to swell in 600 ml of water and 200 ml of acetone. 7 g of iodine in 100 ml of ethanol were added to the swelled gel, while stirring. The stirring was continued for 60 minutes at 35° C. The iodophor gel obtained was filtered off and dried at room temperature for 12 h and then at 40° C for 48 h.

Yield: 105 g. Analysis: 6.12 % iodine and 10.90 % moisture; ion exchange capacity: 3.1 meq/g; swelling capacity: 6.6 ml/g; extraction test: 2.00 g iodophor.
first extraction: release of 1.9 % iodine
second extraction: release of 2.0 % iodine
third extraction: release of 2.0 % iodine
fourth extraction: release of 1.4 % iodine
fifth extraction: release of 1.4 % iodine
sixth extraction: release of 1.5 % iodine
seventh extraction: release of 1.4 % iodine.

EXAMPLE 13

100 g of a commercially available carboxymethyl substituted dextran gel (CM-Sephadex C-25, Pharmacia Fine Chemicals, Uppsala, Sweden) having a particle size of 40 - 120 $\mu$ and a cation exchange capacity of 4.6 meq/g were allowed to swell in 600 ml of water and 200 ml of aceton. A solution of 10 g of iodine in 100 ml of ethanol was added to the swelled gel, while stirring. The stirring was continued for 60 minutes at room temperature. The iodophor gel obtained was filtered off and dried at room temperature for 16 h and subsequently at 40° C for 48 h.

Yield: 98 g. Analysis; 0.25 % iodine and 9.58 % mositure; cation exchange capacity: 4.1 meq/g; swelling capacity: 7.5 ml/g; extraction test: 3.01 g — 1 extraction — 56 %.

EXAMPLE 14

A disinfective skin and wound cream was prepared by mixing the following components:

| | |
|---|---|
| 3 g of the iodophor according to Example 2, sieved to a particle size <100$\mu$ and swelled in 28 g of water | 31 g |
| Paraffin | 10 g |
| Lanolin | 10 g |
| Vaseline | 24 g |
| Silicon oil | 2 g |
| Wool wax alcohols | 1 g |
| Cetanol | 1 g |
| Zinc oxide | 24 g |
| Total | 103 g |

EXAMPLE 15

A viscous suspension suitable for the disinfection of wound pockets and fistulas was prepared as follows:

5 g of the iodophor prepared according to Example 2 (sieved to a particle size <100 $\mu$) was allowed to swell in 25 ml of physiological sodium chloride solution. The suspension obtained is preferably administrated by means of a syringe cannula.

EXAMPLE 16

The iodophor prepared according to Example 10 (particle size 100 – 300 $\mu$) was used (clinically) for the disinfection of open wounds. The iodophor powder was applied to the wounds by means of a salt sprinkler. The healing of the wounds was improved without any undesirable side-effects observed.

What is claimed is:
1. A disinfectant containing up to 20% iodine in complexed form, wherein iodine is complexed to a hydrophilic organic carrier, which
is a cross-linked polymerisation product of a polyhydroxylic organic material and a bi-functional cross-linking agent, which forms a three dimensional lattice, kept together by covalent bonds, and which is insoluble in water, but capable of swelling in water to form a gel, the swelling capacity of the carrier being such that 1 g of the dry carrier forms a gel having a volume of from 2 to 100 ml when completely swelled in water.

2. A disinfectant according to claim 1, wherein the carrier of the iodine complex is substituted at available hydroxy sites with ion exchange groups selected from the group consisting of sulphoethyl groups, carboxymethyl groups and diethylaminoethyl groups.

3. A disinfectant according to claim 1, wherein the carrier of the iodine complex is a polymerisation product obtained by cross-linking of a polyhydroxylic organic material by means of a bi-functional organic cross-linking agent of the type Y-R-Z, wherein Y and Z represent epoxy groups or halogen atoms and R is an aliphatic organic residue lacking dissociating group.

4. A disinfectant according to claim 3, wherein the bi-functional cross-linking agent is selected from the group consisting of epihalogenohydrins, dihalogenohydrins, 1:2, 3:4-diepoxybutane, diepoxy-propylether and diepoxy-propylethers of ethylene, propylene and polyethylene glycol.

5. A disinfectant according to claim 1, wherein the polyhydroxylic organic material is selected from the group consisting of monosaccharides, disaccharides, polysaccharides, partial degradation products thereof, synthetic polyhydroxylic polymers, and sugar alcohols.

6. A disinfectant according to claim 5, wherein the polyhydroxylic organic material is selected from the group consisting of starch, dextran, dextrin, cellulose, polyvinyl alcohol, saccharose, and sorbitol.

7. A disinfectant according to claim 1, wherein additional iodine is also absorbed or adsorbed to the carrier.

* * * * *